United States Patent [19]
Domingues

[11] Patent Number: 5,514,386
[45] Date of Patent: May 7, 1996

[54] DOUGH COMPOSITIONS CONTAINING TEMPERATURE SENSITIVE YEAST AND A TEMPERATURE SENSITIVE YEAST STRAIN AND PROCESS OF MAKING

[75] Inventor: David J. Domingues, Plymouth, Minn.

[73] Assignee: The Pillsbury Company, Minneapolis, Minn.

[21] Appl. No.: 329,667

[22] Filed: Oct. 26, 1994

Related U.S. Application Data

[63] Continuation of Ser. No. 32,219, Mar. 19, 1993, abandoned, which is a continuation-in-part of Ser. No. 829,453, Jan. 31, 1992, abandoned, which is a continuation-in-part of Ser. No. 732,081, Jul. 18, 1991, abandoned.

[51] Int. Cl.$^6$ .................................................. A21D 10/02
[52] U.S. Cl. ................................... 426/8; 426/19; 426/27; 426/60; 426/549
[58] Field of Search .................................. 426/8, 60, 19, 426/27, 549

[56] References Cited

U.S. PATENT DOCUMENTS

| | | | |
|---|---|---|---|
| 1,811,772 | 6/1931 | Willoughby | 426/8 |
| 2,478,618 | 8/1948 | Armstrong et al. | 426/128 |
| 4,346,115 | 8/1982 | Clement et al. | |
| 4,350,710 | 9/1982 | Sundermann | 426/19 |
| 4,357,356 | 11/1982 | Joulin | 426/19 |
| 4,381,315 | 4/1983 | Yong et al. | |
| 4,547,374 | 10/1985 | Nakatomi et al. | |
| 4,693,898 | 9/1987 | Nakatomi et al. | |
| 4,792,456 | 12/1988 | Katz et al. | |

FOREIGN PATENT DOCUMENTS

| | | |
|---|---|---|
| 0442575 | 8/1991 | European Pat. Off. |
| 1007280 | 10/1965 | United Kingdom |
| 1587296 | 4/1991 | United Kingdom |

OTHER PUBLICATIONS

Hino, et al., "New Freeze–Tolerant Yeast for Frozen Dough Preparations", 6031 *Cereal Chemistry* 64(4):269–275.
Singh, et al., "Growth Analysis of Mutations Affecting Growth of *Saccharamyces Cerevisiae* at Low Temperature," *Genetics*, 77:651–659 (Aug. 1974).
Ursic, et al., "A Cold–Sensitive Mutant of *Saccharomyces Cerevisiae* Defective in Ribosome Processing", *Molec. gen. Genet.* 175, 313–323 (1979).
Finney, "A Review of Older and Some Newer Short–Time Bread Baking Studies," *The Bakers Digest*, vol. 51, No. 5, Oct. 1977, pp. 81–86.
Harrison, et al., "Phosphlipid Breakdown in Baker's Yeast During Drying", *Nature* [200] pp. 1189–1190 (1963).
Herrera, et al., "Loss of Cell Constituents On Reconstitution of Active Dry Yeast", *Arch. Biochem. and Biophys.* [63] 131–143 (1956).
Banwart, *Basic Food Microbiology*, 1981, AVI:Westport, Connecticut, pp. 418–441.

*Primary Examiner*—Helen Pratt
*Attorney, Agent, or Firm*—Edward Hotchkiss; Janal M. Kalis; Aleya Rahman

[57] ABSTRACT

The present invention includes a method of making a refrigeratable dough composition that includes a step of heating the dough to at least a threshold inactivation temperature of yeast in the dough to substantially inactivate the yeast substantially without baking dough. The present invention also includes a yeast strain of the genus-species *Saccharomyces cerevisiae* characterized by a thermally labile pyruvate kinase enzyme activity that substantially prevents anaerobic growth by the yeast strain at or above about 36° C.

19 Claims, 1 Drawing Sheet

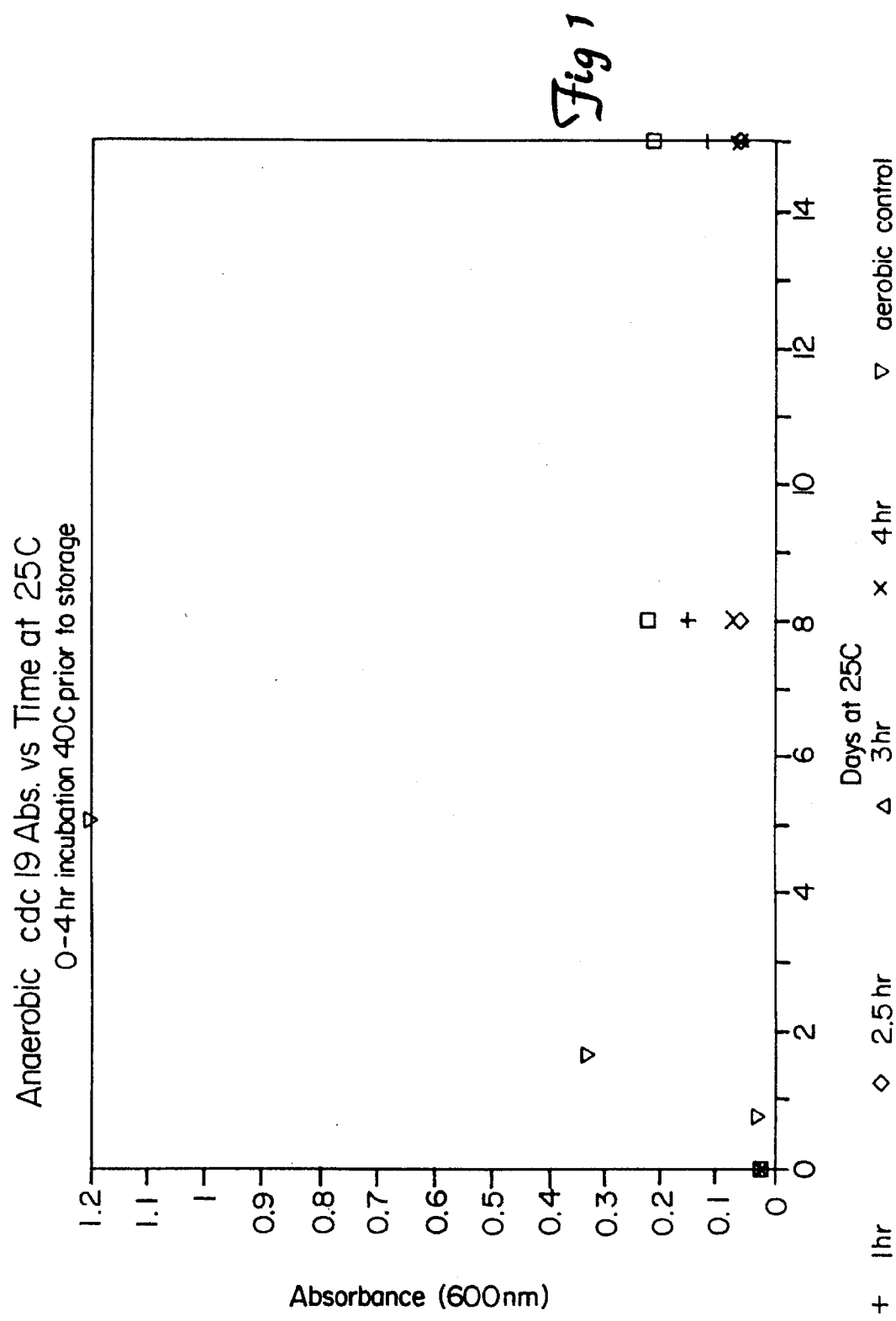

5,514,386

1

DOUGH COMPOSITIONS CONTAINING TEMPERATURE SENSITIVE YEAST AND A TEMPERATURE SENSITIVE YEAST STRAIN AND PROCESS OF MAKING

This Application is a continuation of prior U.S. application Ser. No. 08/032,219, filed Mar. 19, 1993, now abandoned, which is a continuation-in-part of U.S. application Ser. No. 07/829,453, filed Jan. 31, 1992, now abandoned, which is a continuation-in-part of U.S. application Ser. No. 07/732,081, filed Jul. 18, 1991, now abandoned.

FIELD OF THE INVENTION

The present invention relates to refrigerated dough compositions leavened by temperature sensitive yeast and an improved strain of yeast suitable for use in leavening a refrigerated dough composition.

BACKGROUND OF THE INVENTION

Baker's yeast, *Saccharomyces cerevisiae*, is commonly used as a leavening agent in dough, resulting in a baked product having organoleptic qualities such as taste, aroma and texture far superior to those associated with chemically leavened dough products. Commercial dough manufacturers preferably use yeast as a leavening agent as naturally leavened products are desired by consumers. Because consumers prefer the "fresh-baked" characteristics of dough products, many dough manufacturers sell pre-proofed dough in both frozen and refrigerated forms. "Pre-proofed dough" refers to dough which has been subjected to increased temperatures allowing the leavening agent in the dough to generate carbon dioxide sufficient to raise the dough to a desired volume. Proofing the dough before distributing it to consumers eliminates the need for the consumers to carefully proof the dough for an extended period of time before baking it. Refrigerated doughs are particularly convenient as they require no thawing and therefore can be baked into the desired product more rapidly than frozen doughs. Refrigerated doughs have a disadvantage compared to frozen doughs, however, in that the use of yeast as a natural leavener has not yet been successful in refrigerated doughs which need to be stored for any extended periods of time.

Examples of refrigerated dough compositions are described in Yong et at., U.S. Pat. Nos. 4,381,315 and 4,383,336; and Atwell, U.S. Pat. No. 4,526,801. Refrigerated doughs are prepared by combining the dough ingredients including a leavening agent, optionally placing the dough in containers, proofing the dough, and then storing the dough at refrigeration temperatures, i.e. between about 0° C. and about 12° C.

Refrigerated doughs are most commonly packaged prior to storage and may be packed prior to proofing the dough, in which case the dough is proofed in a closed container until the volume of the dough fills and seals the container. Alternatively, the dough may be packaged in flexible packaging after it has been proofed, in which case a sealing means is applied to the package in which the dough has been packed to render the package airtight. For purposes of this disclosure, the expression "containing means" will hereinafter be used to refer to both rigid containers and flexible packaging.

Depending on the product, storage temperature and the like, the minimum acceptable shelf life of commercially produced refrigerated doughs can be as long as about 90 days. At refrigeration temperatures, conventional yeast continue to produce carbon dioxide, causing the dough to continue rising and the dough ingredients to continue reacting, even after the dough has been packaged in a sealed containing means for storage. Because conventional yeast continue to produce carbon dioxide at refrigeration temperatures, overfermentation of the dough occurs, resulting in adverse changes in the dough theology. These changes negatively affect the taste, aroma, texture and other organoleptic qualities of the baked or cooked product prepared from the dough.

If the dough is packaged in a sealed containing means for storage at refrigeration temperatures, the continued carbon dioxide production by conventional yeast causes a continuous increase in the pressure within the containing means. Ultimately, the pressure inside the containing means increases to a point where the containing means raptures. This rupture can occur with conventional yeast in a matter of a week or less, which is well below the minimum acceptable shelf life for most commercially produced refrigeratable doughs.

For these reasons, refrigerated dough manufacturers generally have been unable to use yeast as the leavening agent in refrigerated doughs. Dough manufacturers rely instead on less preferred chemical leavening agents which comprise a combination of a leavening acid and a leavening base that react with one another to generate carbon dioxide. Chemical leavening permits control of the leavening process through controlling the quantity of reactants and the resulting volume of carbon dioxide. Use of chemical leavening agents usually eliminates the problems associated with conventional yeast such as overfermentation and container rupture by buildup of internal pressure, but the organoleptic qualities such as taste, aroma and texture of baked goods made from chemically leavened doughs are notably inferior to those of a yeast-leavened dough product. To improve the taste and aroma of chemically leavened dough products, yeast flavoring, such as inactive pasteurized yeast culture, may be added to chemically leavened dough. The flavor and texture of the products resulting from these doughs, however, remain inferior to yeast-leavened dough products.

Thus, there has been a long-felt but unsatisfied need in the field of refrigerated dough products to provide a refrigeratable yeast-leavened dough. It would be advantageous to provide a yeast-leavened dough which can be stored at refrigeration temperatures for extended periods of time without significantly adversely affecting the quality of the dough. It would also be desirable to provide a dough product, i.e. a dough in a sealed container, which is capable of being stored at refrigeration temperatures for extended periods of time without failure of the containing means.

SUMMARY OF THE INVENTION

The present invention provides dough compositions suitable for refrigeration and methods of making the same. In accordance with the present invention, a dough comprises flour, water and a yeast which is capable of fermenting available substrate at temperatures below a threshold inactivation temperature but which will become substantially inactivated if heated to a temperature substantially equal to or greater than the threshold inactivation temperature. This threshold inactivation temperature is desirably greater than room temperature and less than a temperature at which the dough will begin to cook or bake and become a baked product instead of a dough.

In accordance with a method of the invention, a dough is formed by mixing flour, water and yeast. This dough composition is allowed to proof, and is then heated to a temperature at least as great as the threshold inactivation temperature of the yeast, substantially inactivating the yeast, i.e. rendering the yeast substantially incapable of fermentation at virtually any temperature. The dough may then be stored at refrigeration temperatures without any further significant proofing of the dough.

This invention further provides a temperature-sensitive yeast which is well suited for use as the leavening agent in refrigerated dough compositions. This yeast has a threshold inactivation temperature above which the yeast is substantially inactivated, such as by being rendered an obligate aerobe. Once being heated above the threshold inactivation temperature, the yeast will remain substantially inactive at virtually any temperature if maintained in a substantially anaerobic environment. In another embodiment, the yeast is sensitive to both unduly high and unduly low temperatures. Even if a limited quantity of oxygen is present in the environment, the yeast will remain substantially inactive at refrigeration temperatures because of its sensitivity to low temperatures.

BRIEF DESCRIPTION OF THE DRAWINGS

FIG. 1 shows a graphical view of an absorbence vs. time at 25° C. for a mutant species of *Saccharomyces cerevisiae*, CDC 19.

DETAILED DESCRIPTION OF THE INVENTION

The present invention provides a dough composition containing yeast as the leavening agent, the resulting dough having an extended shelf life under refrigeration conditions. The present invention further provides yeast to be used in the dough compositions. The yeast used in this composition are temperature sensitive. If they are heated above a threshold inactivation temperature of the yeast, the yeasts carbon dioxide producing capabilities in substantially anaerobic environments are substantially inactivated at essentially all temperatures. By effectively controlling the production parameters and the yeast's carbon dioxide producing capabilities, the proofing of dough compositions by yeast can be regulated.

As explained above, even at refrigeration temperatures, conventional yeast can continue to produce carbon dioxide. If carbon dioxide production is substantially inactivated by heating the dough composition above the yeasts threshold inactivation temperature, the amount of proofing can be controlled once the dough has reached a predetermined volume, regardless of the subsequent temperature conditions to which the dough composition is exposed.

Refrigerated dough compositions of the present invention employ temperature sensitive strains of yeast which function normally at temperatures below their threshold inactivation temperatures. For instance, the yeast may be capable of fermenting substrate in the dough at about room temperature and can continue to ferment substrate at temperatures below the threshold inactivation temperature. However, once the yeast is heated above the threshold inactivation temperature it loses its ability to produce carbon dioxide required for proofing the dough. It has been surprisingly discovered that by using these temperature sensitive yeast, the dough compositions may be anaerobically proofed to a predetermined volume, then heated to at least the threshold inactivation temperature to substantially inactivate the yeast's carbon dioxide producing capabilities. In some dough compositions, the proofing of the dough may be carried out while heating the dough up to the threshold inactivation temperature. The dough composition may then be stored, e.g. at refrigeration temperatures, for extended periods of time without the disadvantages associated with excess carbon dioxide production and degradation of dough theology by conventional yeast during storage.

The refrigeratable dough composition of the invention may optionally be placed in containing means for storage at refrigeration temperatures. Such containing means are known to those skilled in the art and include spiral wound composite cans. Unproofed dough is placed in the can which is then closed, proofed to an internal pressure to about 15–20 p.s.i. thereby filling the entire volume of the can with dough. The dough creates a seal in said containing means by filling vents and thus rendering the internal environment of the can substantially anaerobic. Examples of such spiral wound composite cans suitable for refrigerated dough include those described in the following patents, the teachings of which are incorporated by reference herein: Culley et at., U.S. Pat. No. 3,510,050; Reid, U.S. Pat. No. 3,972,468; and Thomhill et at., U.S. Pat. No. 3,981,433.

An alternate containing means is formed of a flexible packaging material, such as a polymeric film, and the internal environment of the containing means is substantially anaerobic. One method for making the internal environment substantially anaerobic is by hermetically sealing the containing means under a vacuum or in an inert gas environment. Alternatively, an inert gas may be added to the package, substantially flushing oxygen from the containing means, prior to sealing.

The refrigerated dough composition of the present invention may alternatively be stored without a containing means at refrigeration temperatures directly after cessation of proofing.

The formulation of the dough composition is not critical; virtually any dough comprising flour, water and a yeast in accordance with the invention may be used. An example of one dough composition formulation suitable for use in the present invention is provided in Table I:

TABLE I

| Ingredient | Weight Percent of Dough |
| --- | --- |
| flour | 54.53–57.93 |
| water | 34.71–35.45 |
| gluten pre-blend* | 3.88–3.91 |
| dextrose | 0.99 |
| salt | 0.75 |
| temperature sensitive yeast | 1.00 |

*The gluten pre-blend comprises about 75% vital wheat gluten; 21.9% hard, high gluten; enriched ingredient flour; 2.5% xanthan gum; and 0.616% azodicarbonamide premix.

The temperature sensitive yeast used in one embodiment of the present invention may be any member of the species *Saccharomyces cerevisiae* which have a threshold inactivation temperature, i.e., which are substantially inactivated if heated to a temperature above some threshold. The threshold inactivation temperature of the yeast is optimally no more than about 43° C., at which temperature conventional dough made with wheat flour will usually begin to bake. (As used herein, the term "dough" or "dough composition" refers to an unbaked dough, while a dough which has been baked is referred to as a "baked dough", "baked product" or the like.)

On the other hand, if the threshold inactivation temperature of the yeast is below room temperature, making the dough in a commercial operation may be unduly difficult because the entire production area would likely have to be maintained below that temperature in order to permit the dough to be proofed by the yeast before it is inactivated. Accordingly, in a preferred embodiment the threshold inactivation temperature of a yeast used in a dough of the invention is between about 25° C. and about 43° C.

It has also been found that heating a dough above about 40° C. for a significant period of time can be harmful to the dough due to possible deactivativation and denaturation of wheat flour gluten, as well as promotion of the growth of spoilage microorganisms native to wheat flour, at highher temperatures. As explained more fully below, the yeast is allowed to proof the dough before it is heated above the threshold inactivation temperature. Proofing takes place more quickly at elevated temperatures, e.g. about 30°–40° C., than it does at room temperature or below; the activity of the yeast, and hence the rate of proofing, can be said to be roughly positively correlated with temperature.

It would therefore be advantageous in a commercial production environment to be able to heat the dough above room temperature, e.g. to about 30° or more, without exceeding the threshold temperature of the yeast and rendering it substantially inactive. Hence, in a particularly preferred embodiment of the invention the threshold inactivation temperature of the yeast is desirably between about 25° C. and about 40° C., and optimally between about 30° C. and about 40° C.

Such temperature sensitive yeast desirably enter cell cycle arrest when exposed to temperatures above their threshold inactivation temperatures. Applicants have discovered that once the temperature-induced cell cycle arrest occurs, the yeast tend to become obligate aerobes and are rendered substantially incapable of fermentative anaerobic growth. Applicants have further discovered that these characteristics can be used to effectively control dough proofing and that dough containing such temperature sensitive yeast may be stored under refrigeration conditions for extended periods of time.

By using temperature sensitive yeast in dough compositions, the dough can be proofed to the desired volume at temperatures below the threshold inactivation temperature, following which the yeast can be substantially inactivated by subjecting the dough, and hence the yeast therein, to temperatures above the yeast's threshold inactivation temperature. The dough thus prepared can be refrigerated for extended periods of time without the risks of overfermentation and rupture of optional containing means by excess proofing of the dough composition.

Following the inactivation of the yeast, allowing the dough composition temperatures to change, even to temperatures below the threshold levels, has no measured effect on the substantial inactivation of the yeast's fermentative capabilities. These characteristics of the dough make it especially suitable for transportation and storage where large temperature fluctuations are possible, which could have deleterious effects on dough leavened with conventional, non-temperature sensitive yeast. The product obtained by baking or cooking this refrigerated dough composition can be defined as a bread product as it is leavened with yeast and has the desired organoleptic qualities associated with yeast-leavened dough products.

Given the present disclosure, it will be well within the ability of those skilled in the art to make yeasts which can be substantially inactivated at by heat treatment at elevated temperatures. Such yeasts can be made through standard methods of crossing yeast strains, isolating suitable strains having the desired properties and the like. These types of common techniques are described, for example, by Sherman et al. in *Methods in Yeast Genetics,* the teachings of which are incorporated herein by reference. Of particular interest in the Sherman et al. is Section III, entitled "Making Mutants", which appears on pages 273–369 of this reference.

One process for creating and isolating such mutants has been taught by Hartwell et al. in "Genetic Control of the Cell Division Cycle Mutant in Yeast: V. Genetic Analysis of cdc Mutants", *Genetics* 74: 367–286 (June, 1973), the teachings of which are incorporated herein by reference. As disclosed in that article, Hartwell et al. treated a strain of yeast having the genotype a ade1 ade2 ura1 tyr1 his7 lys2 gal1, identified as swain A364A, with a known mutagene, namely either N-methyl-N'-nitro-N-nitrosoguanadine or ethylmethane sulfonate. Resulting temperature-sensitive mutants having a permissive temperature of about 23° C. and a restrictive growth temperature of about 36° C. were isolated. Of these temperature-sensitive mutants, cell division cycle mutants were isolated by identifying morphological criteria for these mutants and selecting those mutant colonies in which 80 % or more of the cells exhibited a uniform morphology.

Following this process, Hartwell et al. identified nearly 150 different cdc mutants. Complementation studies demonstrated that these mutants defined 32 complementation groups, with 30 of those groups defined by single mutations in nuclear genes (as determined by standard genetic analysis techniques). One such strain which has been found to work well exhibited a structural mutation in the pyruvate kinase gene, but it is to be understood that there may be other thermally sensitive mutations which can work well in the present invention.

One possible mechanism for thermal inactivation has been elucidated for the *S. cerevisiae* strain cdc19, available from the Yeast Genetic Stock center at the Donner Laboratory in the Department of Molecular and cell Biology at the University of California, Berkeley (YGSC) and deposited with the American Type Culture Collection, of 12301 Parklawn Drive, Rockville, Md. (ATCC) on 5 Mar. 1993 under the number ATCC 74217. The fermentation pathway of cdc19 yeast strain is substantially inactivated following exposure to temperatures above the threshold inactivation temperature due to a mutation in the yeast that results in a thermally labile pyruvate kinase enzyme. Mutants having a mutation in the pyruvate kinase gene can be identified by known morphological or genetic analysis techniques.

If the dough composition containing the temperature sensitive yeast is subjected to temperatures above the threshold inactivation temperature, pyruvate kinase is rendered structurally inactive and the yeast become obligate aerobes, incapable of virtually any significant anaerobic fermentation until pyruvate kinase biosynthesis resumes. In the cdc19 strain, pyruvate kinase biosynthesis resumes when i) oxygen is present and de novo biosynthesis of pyruvate kinase can occur, or ii) the genetic mutation reverts to the wild type. Such reversions generally may occur only when the yeast are growing. As seen in FIG. 1, wherein the anaerobic growth of such temperature sensitive yeast was observed at 25° C. following 0–4 hours of incubation at 40° C., once the cdc19 cells have been exposed to temperatures above their threshold inactivation temperatures, Under anaerobic conditions the yeast lose the ability to grow and thereby revert to the wild type.

The thermal inactivation of cdc19 yeast substantially eliminates any further carbon dioxide production under anaerobic conditions at all relevant temperatures (e.g.

between about 0° C., when the dough is frozen, and about 45° C., when the dough is baking). This makes the yeast particularly suitable for refrigerated dough compositions in accordance with the present invention.

In a second embodiment of the present invention, the temperature sensitive yeast used in the dough compositions as outlined above may be any member of the species *S. cerevisiae* having an upper threshold inactivation temperature and which becomes substantially inactive at refrigeration temperatures. Such a yeast could be obtained by mating low temperature sensitive yeast to high temperature sensitive yeast, for example. There are numerous yeast strains that carry low temperature sensitive mutations. For purposes of the present invention, the choice of which of these mutant strains are utilized is not believed to be critical as long as the requisite characteristics of substantial inactivity at refrigeration temperatures and substantially normal fermentative activity at elevated temperatures, i.e above refrigeration temperatures, are observed in the particular strain chosen.

Low temperature sensitive mutants are sometimes found in normal yeast strains. Isolation of these low temperature sensitive mutants may be accomplished by a variety of methods known to those skilled in the art. One isolation method is the "tritium suicide" enrichment protocol described by Littlewood and Davies in "Enrichment for Temperature Sensitive and Auxotrophic Mutants in *Saccharomyces cerevisiae* by Tritium Suicide," *Mutation Research* Volume 17, pp. 315–322 (1973), the teachings of which are incorporated herein by reference.

In this protocol, a strain of yeast is first placed in a growth medium at normal permissive temperature followed by reduction of the temperature to refrigeration (non-permissive) temperature. Tritiated uridine or tritiated amino acids are supplied to the culture. Yeast cells remaining active at these temperatures incorporate the tritiated precursors and are killed by the tritium. Those cells that are inactive at these lower temperatures do not incorporate the toxic precursors and are able to survive the low temperatures by virtue of their low temperature sensitivity.

One skilled in the art could readily make a low temperature sensitive yeast in accordance with this tritium suicide process. However, the following strains of yeast which become substantially inactive at refrigeration temperatures are available to the public from the ATCC: "lts1" *S. cerevisiae* (Designation No. ATCC 74124), "lts2" *S. cerevisiae* (Designation No. ATCC 74125), "lts3" *S. cerevisiae* (Designation No. ATCC 74126), "lts4" *S. cerevisiae* (Designation No. ATCC 74127), "lts5" *S. cerevisiae* (Designation No. ATCC 74128), "lts6" *S. cerevisiae* (Designation No. ATCC 74129), "lts7" *S. cerevisiae* (Designation No. ATCC 74130), and "lts8" *S. cerevisiae* (Designation No. ATCC 74131 Deposits to the ATCC were made in accordance with the Budapest Treaty on the International Recognition of the Deposit of Micro organisms for the Purposes of Patent Procedure).

Mating a high temperature sensitive yeast strain with a low temperature sensitive yeast strain can be performed by any means known to produce haploid mutants in yeast. One such protocol is derived from *Methods in Yeast Genetics, A Laboratory Course Manual*, Cold Spring Harbor Laboratory Press, pp. 53–59 (1990), the teachings of which are incorporated by reference herein.

Applicants have discovered that combining the properties of a high temperature sensitive yeast strain with a low temperature sensitive yeast strain results in a mutant yeast strain with characteristics that make it excellent for use as a leavening agent in refrigerated dough compositions. By combining the high and low temperature sensitivities in the yeast, not only can the yeast be inactivated by raising the temperature of the dough composition above the threshold inactivation temperature, but the remote possibility of some yeast cells not becoming inactivated and continuing to generate carbon dioxide at lower temperatures such as refrigeration temperatures is also eliminated by introducing low temperature growth sensitivity into the yeast strain.

One possible mechanism for the low temperature growth sensitivity in low temperature sensitive yeast has been elucidated for "lts 8" *S. cerevisiae* (noted above). The mutation carried by this strain renders the yeast incapable of any protein synthesis at lower temperatures such as refrigeration temperatures. These yeast, therefore, cannot grow below their threshold inactivation temperatures.

The combination of the characteristics of the high and low temperature sensitive yeast makes pyruvate kinase biosynthesis highly unlikely after the temperature of the yeast in the dough composition has been raised above its threshold inactivation temperature followed by refrigeration, which substantially inactivates virtually all protein synthesis as a result of the low temperature sensitive mutation. Since pyruvate kinase is substantially inactivated, and pyruvate kinase cannot be synthesized de novo by the yeast in any significant quantities, virtually all anaerobic fermentative growth is eliminated and no significant volume of carbon dioxide will be produced by the yeast. The low-temperature sensitive mutation of the yeast thus serves a safety function—if some oxygen is inadvertently permitted to come into contact with the yeast (e.g. if a container of dough leavened with this yeast allows air to leak in), the yeast still will be substantially unable to produce carbon dioxide.

In accordance with a method for making a dough composition in accordance with the present invention, the temperature sensitive yeast is mixed with water and a flour product, such as ground wheat, in suitable proportions to form a dough which is suitable for baking. Additional ingredients necessary to achieve a desired texture or taste in the final, cooked dough product may be added during this mixing as well. Such ingredients are commonly known in the art and include salt, sugars, wheat gluten, dough conditioners and other flavorings. All of these ingredients should be thoroughly mixed together to ensure a uniform dough composition; a wide variety of means for mixing doughs are well known in the art and need not be discussed in detail here.

Once the dough is mixed, the yeast should be allowed to generate carbon dioxide to proof the dough. This proofing may be carded out at any suitable temperature. However, if the above-described yeast having low-temperature sensitivity is used, the proofing should be carried out at temperatures greater than refrigeration temperatures as the yeast remains substantially inactive at such temperatures. In order to reduce production time in a commercial operation, it may be advantageous to heat the dough to a temperature greater than room temperature to speed up carbon dioxide production. The dough may therefore be heated for proofing, but care should be taken to remain below the threshold inactivation temperature throughout most of the dough in order to avoid inactivating the yeast before proofing is completed. In one embodiment which has been found to work well using the cdc19 yeast described below, which has a threshold inactivation temperature of about 36° C., proofing is carried out at a temperature between about 30° C. and about 35° C.

Once the dough has been proofed to a predetermined degree, the temperature of the dough may be elevated up to, or desirably above, the threshold inactivation temperature. The dough will not heat to a uniform temperature instantly; there will tend to be a temperature gradient in the dough due to the low coefficient of thermal transfer of doughs, with the outer portion of the dough being at a temperature closer to the ambient temperature than the inner portion of the dough. The dough is optimally heated slowly enough or held at a temperature at or above the threshold inactivation temperature long enough to ensure that most, and preferably substantially all, of the yeast in the dough reaches the threshold and is substantially inactivated.

The resulting yeast can be then stored at refrigeration temperatures for an extended period of time without generating any significant additional volume of carbon dioxide. As the term is used herein, refrigeration temperatures are between about 0° C. and about 12° C., with a temperature range of about 4° C. to about 7.2° C. being preferred. The dough may be stored at such temperatures for upwards of about 90 days, which is the minimum acceptable shelf life for most commercially produced refrigeratable doughs, without any undue deterioration in quality.

In accordance with a further embodiment of the present method, the dough is packaged in a container means such as that described above. It is preferred that the dough be placed in the container means prior to proofing and be proofed in the container means. In current commercial packaging operations using spirally wound cans, the dough is placed in the container and proofed until the internal pressure in the can reaches about 15–20 psi. In accordance with the present invention, the dough is placed in the container and is allowed to proof until the internal pressure of the container means reaches about 15–20 psi, at which point the dough is heated above the threshold inactivation temperature to substantially inactivate the yeast. The packaged dough product may then be stored at refrigeration temperatures for an extended period of time.

As noted above, there may be temperature gradients in the dough which can produce a lag time between an ambient temperature change and a change in the temperature of the center of the dough. The temperature profile of the proofing and inactivation process should be designed to take this lag time into account. In some instances, the lag time may be sufficient to enable the dough to be proofed at an elevated temperature at the same time as the dough is being heated up to the threshold inactivation temperature of the yeast. In such an embodiment of the present method, the temperature profile of the heat treatment may be smooth, i.e. not exhibit a sharp demarcation between the proofing and the inactivation steps.

EXAMPLE I

Preparation of High and Low Temperature Sensitive Yeast

A strain of yeast having a sensitivity to high temperatures, i.e. which is substantially inactivated at elevated temperatures, was crossed with a low temperature sensitive yeast, i.e. a yeast which becomes substantially inactive at low temperatures, but may retain the ability to ferment substrate at higher temperatures. The yeast sensitive to high temperatures was a mutant strain of *Saccharomyces cerevisiae* designated cdc19 and deposited with the ATCC on 5 Mar. 1993 under the number ATCC 74131. This particular strain of yeast has a threshold inactivation temperature of approximately 36° C. and is rendered an obligate aerobe if heated at or above that temperature.

The low temperature sensitive yeast strain used is the lts8 yeast deposited with the ATCC under deposit number ATCC 74131, as mentioned above. Yeast mutant strain lts8 is representative of many known low temperature sensitive yeast strains which behave substantially normally at elevated temperatures, e.g. can ferment available substrate at room temperature or greater, but become substantially inactive at refrigeration temperatures.

The high and low temperature sensitive mutant yeast strain was obtained by mating the high temperature sensitive mutant strain cdc19 with the low temperature sensitive mutant strain lts8. The protocol used to mate these strains was derived from *Methods in Yeast Genetics, A Laboratory Course Manual*, Cold Spring Harbor Laboratory Press, pp. 53–59 (1990), as follows:

Six substantially parallel lines were drawn on a white sheet of cardboard. For each of the cdc19 and lts8 strains, a YEPD (YEP plus dextrose) plate was placed over the striped pattern. Using a sterile loop, the strains were streaked onto their respective plates using the parallel lines as a guide and allowed to incubate at approximately 25° C. for about 24 hours.

An impression of the cdc19 strain was made on a replicate plate pad. This impression was imprinted onto a fresh YEPD plate. Using a fresh replicate plate pad, an impression of the low temperature sensitive lts8 strain was made. The second replicate pad was imprinted on the same YEPD plate used for the previous imprinting, but at an orientation generally perpendicular to the first imprint, resulting in a pattern of yeast strains resembling a checkerboard. This doubly imprinted YEPD plate was incubated at approximately 25° C. overnight (i.e about 12–15 hours).

The YEPD plate thus prepared was imprinted on a synthetic dextrose minimal media (SD) plate containing about 6.7 g of bacto-yeast nitrogen base without amino acids, about 20 g glucose and about 20 g bacto-agar per liter of distilled water. The SD plate was incubated for about two days at about 25° C. Growth at the intersections of the "checkerboard" pattern was scored and plated onto a SD fresh plate to isolate the diploid (crossed) colonies from the haploid colonies. The diploid colonies isolated on the SD plate were streaked onto a plate of sporulation media (as formulated below) and incubated for days at about 25° C.: about 10 g (1 wt. %) potassium acetate, about 1.0 g (0.1 wt. %) bacto-yeast extract, about 0.5 g (0.05 wt. %) glucose, about 20 g (2.0 wt. %) bacto-agar, with the balance being about 1000 ml distilled water.

About one loopful of yeast cells was taken from the sporulation plate and combined with about 300 microliters distilled water and approximately 15 microliters glusulase in an Eppendorf™ microfuge tube. This solution was mixed by vortex and incubated at around 30° C. for approximately 30 minutes. The incubated sample was briefly sonicated to separate spore clusters. Serial dilutions of about $10^{-4}$, $10^{-5}$ and $10^{-6}$ of the sonicated sample were plated onto YEPD and stored at approximately 25° C. for about two days.

Three replicate plates were prepared from each of the $10^{-5}$ and $10^{-6}$ dilution plates, with one of the three plates from each dilution being stored at about 12° C., another at about 25° C., and the third plate from each dilution being stored at about 38° C. These plates are incubated for 4 days at their respective temperatures. cdc19×lts8 haploid colonies should only grow at 25° C. as their high temperature sensitivity substantially prevents growth at 38° C. and the low teperature sensitivity will reduce the yeast's growth ram to a very low rate at about 12° C.

The growth rate of the cdc19 strain, the lts8 strain and the cdc19×lts8 strain produced as outlined above were compared at about 12° C., about 25° C. and about 38° C. The cdc19 yeast was able to grow well at both about 12° C. and about 25° C., but was substantially unable to grow at about 38° C. The lts8 yeast was able to grow at all three temperatures, but this is to be expected because the lts8 strain does not substantially cease activity until the temperature drops below about 10° C. However, the growth of the lts8 yeast at about 12° C. is less vigorous than that of the cdc19 strain. The cdc19×lts8 yeast grew very poorly at about 12° C., grew fairly well at about 25° C., and was substantially unable to grow at about 38° C. The CDC 19×LTS8 yeast was deposited with the ATCC and was received by the ATCC on Mar. 15, 1993. The yeast was deposited with the ATCC and given deposit number ATCC 74217 in accordance with the Budapest Treaty on the International Recognition of the Deposit of Microorganisms for the Purposes of Patent Procedure.

Although the present invention has been described with reference to preferred embodiments, the invention is not to be limited to those embodiments described herein except to the extent that such limitations are found in the appended claims.

What is claimed is:

1. A method of making a refrigeratable dough composition comprising the steps of:
   a. mixing flour, water and yeast to form a dough;
   b. allowing said yeast to generate carbon dioxide to proof the dough;
   c. heating said dough to at least a threshold inactivation temperature of no more than about 50° C. of the yeast to substantially inactivate the yeast substantially without baking the dough; and
   d. storing said dough at refrigeration temperatures for an extended period of time.

2. A method of manufacturing a refrigeratable dough product comprising the steps of:
   a. mixing flour, water and yeast to form a dough;
   b. packaging said dough in a storage container;
   c. allowing the yeast to generate carbon dioxide to proof the dough in the container;
   d. heating the dough in the container to at least a threshold inactivation temperature of the yeast that is no higher than about 50° C. to substantially inactivate the yeast; and
   e. storing the dough in the container at refrigeration temperatures for an extended period of time.

3. The method of claim 2 wherein the dough is proofed by heating the dough to a temperature above room temperature but below said threshold inactivation temperature.

4. The method of claim 2 wherein the threshold inactivation temperature of the yeast is between about 25° C. and about 43° C. and the yeast is substantially inactivated by heating the dough to a temperature of between about 25° C. and about 43° C.

5. The method of claim 4 wherein the threshold inactivation temperature of the yeast is between about 30° C. and about 40° C. and the yeast is substantially inactivated by heating the dough to a temperature of between about 30° C. and about 40° C.

6. The method of claim 5 wherein the dough is proofed by heating the dough to a temperature of at least about 25° C. but below said threshold inactivation temperature.

7. The method of claim 6 wherein the threshold inactivation temperature of the yeast is at least about 35° C. and the dough is proofed by heating the dough to a temperature of between about 30° C. and about 35° C.

8. A refrigeratable dough comprising flour, water and yeast, the yeast exhibiting the following characteristics:
   (a) capable of proofing dough at growth temperatures between about 12° C. and about 38° C.;
   (b) thereafter being capable of having the proofing process substantially terminated upon an increase in the temperature of the yeast to greater than about 38° C. and not more than about 50° C.;
   (c) upon termination of the proofing process, capable of being stably stored, without substantial further metabolic activity.

9. The dough of claim 8 wherein the yeast is further characterized in that it is initially capable of proofing dough at said proofing temperatures, but remains substantially inactive at refrigeration temperatures.

10. An unbaked, yeast-leavened refrigeratable dough product comprising a dough formed of water, flour and yeast, wherein the yeast is a temperature sensitive yeast that is substantially inactivated within a temperature range of 25° C. to 43° C., and is an obligate aerobe.

11. The dough product of claim 10 further comprising a container means for packaging the dough.

12. A dough composition comprising yeast strain of the genus-species *Saccharomyces cerevisiae* characterized by a thermally labile pyruvate kinase enzyme activity that substantially prevents fermentative anaerobic growth of the yeast strain at or above about 36° C.

13. The yeast strain of claim 12, further characterized by obligate aerobic respiration only, once subjected to a temperature of about 10° C. or less.

14. A dough composition containing yeast strain of the genus-species *Saccharomyces cerevisiae* characterized by a thermally labile pyruvate kinase enzyme activity that substantially prevents anaerobic growth by the yeast strain at or above about 36° C. and characterized by obligate aerobic respiration only once exposed to a temperature of about 12° C. or less.

15. The yeast strain of claim 14 deposited with the ATCC having ATCC No. 74217.

16. A dough comprising a yeast strain selected from the genus-species *Saccharomyces cerevisiae* deposited with the ATCC having one of an ATCC number consisting of 74124, 74125, 74126, 74127, 74128, 74129, 74130, 74131, and 74217.

17. A refrigeratable dough system comprising a container and a dough sealed within the container, the dough comprising a yeast having an ATCC No. of 74217, wherein the dough system remains intact when exposed to a temperature at or greater than about 36° C. for at least 14 days.

18. A method of making a dough composition containing a yeast made by a method for making a yeast strain of the genus-species *Saccharomyces cerevisiae* characterized by a thermally labile pyruvate kinase enzyme activity that substantially prevents anaerobic fermentative growth of the yeast strain at or above about 36° C. and further characterized by an obligate aerobic respiration only once exposed to a temperature of about 12° C. or less, comprising:

providing a yeast strain of the genus-species *Saccharomyces cerevisiae* characterized by a thermally labile pyruvate kinase enzyme activity that substantially prevents anaerobic fermentative growth of the yeast strain at or above about 36° C.;

providing a yeast strain of the genus-species *Saccharomyces cerevisiae* characterized by obligate aerobic respiration only once exposed to a temperature of about 10° C. or less;

mating the first yeast strain with the second yeast strain to produce a yeast strain of the genus-species *Saccharomyces cerevisiae* characterized by a thermally labile pyruvate kinase enzyme activity that substantially prevents anaerobic fermentative growth of the yeast strain at or above about 36° C. and further characterized by obligate aerobic respiration only once exposed to a temperature of about 10° C. or less.

19. The method of claim 18 wherein the second yeast strain is deposited with the ATCC and has an ATCC No. within a group consisting of 74124, 74125, 74126, 74127, 74128, 74129, 74130, 74131.

* * * * *